(12) United States Patent
Khoo et al.

(10) Patent No.: US 11,434,224 B2
(45) Date of Patent: Sep. 6, 2022

(54) PROCESSES FOR PREPARING A DIAMINOPYRIMIDINE DERIVATIVE OR ACID ADDITION SALT THEREOF

(71) Applicant: YUHAN CORPORATION, Seoul (KR)

(72) Inventors: Ja-Heouk Khoo, Gunpo-si (KR); Doo-Byung Lee, Yongin-si (KR); Jun-Sup Lee, Yongin-si (KR); Hyun Ju, Hwaseong-si (KR); Woo-Seob Shin, Suwon-si (KR)

(73) Assignee: YUHAN CORPORATION, Seoul (KR)

( * ) Notice: Subject to any disclaimer, the term of this patent is extended or adjusted under 35 U.S.C. 154(b) by 0 days.

(21) Appl. No.: 17/056,557

(22) PCT Filed: May 16, 2019

(86) PCT No.: PCT/KR2019/005859
§ 371 (c)(1),
(2) Date: Nov. 18, 2020

(87) PCT Pub. No.: WO2019/221522
PCT Pub. Date: Nov. 21, 2019

(65) Prior Publication Data
US 2021/0206746 A1    Jul. 8, 2021

(30) Foreign Application Priority Data

May 18, 2018    (KR) .................. 10-2018-0057088

(51) Int. Cl.
*C07D 403/04*    (2006.01)
*C07D 239/47*    (2006.01)

(52) U.S. Cl.
CPC ......... *C07D 403/04* (2013.01); *C07D 239/47* (2013.01); *C07B 2200/13* (2013.01)

(58) Field of Classification Search
CPC ........................... C07D 403/04; C07D 239/47
See application file for complete search history.

(56) References Cited

U.S. PATENT DOCUMENTS

| | | |
|---|---|---|
| 6,846,828 B2 | 1/2005 | Hawley et al. |
| 7,157,580 B2 | 1/2007 | Hawley et al. |
| 9,890,138 B2 | 2/2018 | Lee et al. |
| 10,227,330 B2 | 3/2019 | Lee et al. |
| 2003/0144303 A1 | 7/2003 | Hawley et al. |
| 2005/0107403 A1 | 5/2005 | Hawley et al. |
| 2006/0128726 A1 | 6/2006 | Wang et al. |
| 2008/0293942 A1 | 11/2008 | Cousins |
| 2013/0338179 A1 | 12/2013 | Lee et al. |
| 2018/0111918 A1 | 4/2018 | Lee et al. |

FOREIGN PATENT DOCUMENTS

| | | |
|---|---|---|
| WO | WO-03/040131 A1 | 5/2003 |
| WO | WO-2006/057972 | 6/2006 |
| WO | WO-2012/115480 | 8/2012 |
| WO | 2014/060908 A1 | 4/2014 |

OTHER PUBLICATIONS

Hilfiker, "Polymorphism in the Pharmaceutical Industry", Wiley, Jan. 1, 2006, pp. 1-19.

*Primary Examiner* — Rebecca L Anderson
(74) *Attorney, Agent, or Firm* — Foley & Lardner LLP

(57) ABSTRACT

Provided are a novel process for preparing a diaminopyrimidine derivative or acid addition salt thereof having an activity as a 5-$HT_4$ receptor agonist, crystalline forms of a hydrochloride of the diaminopyrimidine derivative, and processes for preparing the same.

9 Claims, 2 Drawing Sheets

PROCESSES FOR PREPARING A DIAMINOPYRIMIDINE DERIVATIVE OR ACID ADDITION SALT THEREOF

TECHNICAL FIELD

The present invention relates to a novel process for preparing a diaminopyrimidine derivative or acid addition salt thereof having an activity as a 5-$HT_4$ receptor agonist. And also, the present invention relates to novel crystalline forms of a hydrochloride of the diaminopyrimidine derivative and processes for preparing the same.

BACKGROUND ART

The diaminopyrimidine derivative of Formula 1 below has a chemical name of (S)—N-(1-(2-((4-amino-3-nitrophenyl)amino)-6-propylpyrimidin-4-yl)pyrrolidin-3-yl)acetamide. The diaminopyrimidine derivative of Formula 1 or pharmaceutically acceptable salt thereof (e.g., hydrochloride) functions as a 5-$HT_4$ receptor agonist, and therefore can be usefully applied for preventing or treating dysfunction in gastrointestinal motility, one of the gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony (WO 2012/115480).

<Formula 1>

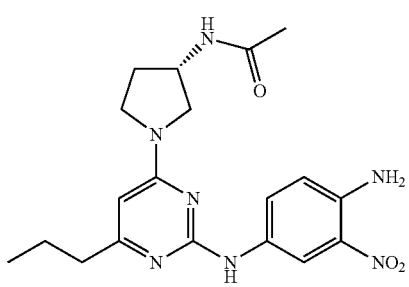

A process for preparing the compound of Formula 1 has been disclosed in WO 2012/115480. Specifically, as shown in the following Reaction Scheme 1, the process for preparing the compound of Formula 1 or pharmaceutically acceptable salt thereof comprises reacting a compound of Formula (I) with $POCl_3$ to prepare a compound of Formula (II); reacting the compound of Formula (II) with a compound of Formula (III) under the presence of a base to prepare a compound of Formula (IV); reacting the compound of Formula (IV) with a compound of Formula (V) to prepare the compound of Formula 1; and optionally converting the compound of Formula 1 to a pharmaceutically acceptable salt thereof.

<Reaction Scheme 1>

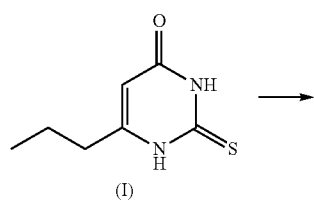

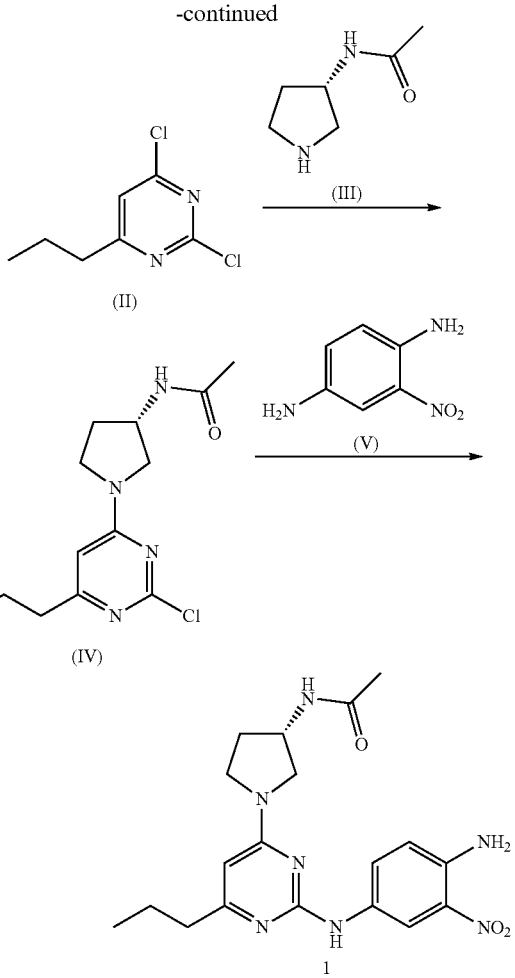

In the process of the Reaction Scheme 1, the compound of Formula (II) is prepared through performing the reaction with an excess $POCl_3$ at a high temperature of 100° C. or higher, thereby producing impurities in high level. Therefore, in order to remove the impurities, said reaction requires performing the purification step using a column chromatography that is unsuitable for industrial mass production. And also, the compound of Formula (II) is obtained in the form of oil; and is readily decomposed at room temperature, thereby bring about stability problems, i.e., low stability.

Especially, since the compound of Formula (II) has two reactive sites (i.e., the 2 and 4 positions of the pyrimidine ring), the structural isomeric impurity that the compound of Formula (III) has been bound to the 2 position of the pyrimidine ring is produced in significant level. Therefore, the reaction of the compound of Formula (II) and the compound of Formula (III) shows very low yield of about 55~60%; and causes the problem that the structural isomeric impurity resides in the final product (i.e., the compound of Formula 1).

And also, in the reaction of the compound of Formula (IV) and the compound of Formula (V), the compound of Formula (V) is known as a material having genetic toxicity. Therefore, in order to avoid the residence of the compound of Formula (V) in the final product (i.e., the compound of Formula 1), there is a problem that the purification step using a column chromatography that is unsuitable for industrial mass production should be carried out.

In addition, WO 2012/115480 has disclosed the step for converting the compound of Formula 1 to a hydrochloride thereof. The converting step comprises reacting the compound of Formula 1 with hydrochloric acid in ethyl acetate, stirring at room temperature for 1 hour, and then filtering the product. It has been found by the present inventors that the hydrochloride of the compound of Formula 1 obtained by said method is in the amorphous form and brings about the problem producing deacetylated impurities in high level when stored at room temperature.

DISCLOSURE

Technical Problem

The present inventors carried out various researches in order to develop a novel process capable of solving the problems of the prior art methods for preparing the compound of Formula 1 or acid addition salt. Especially, the present inventors carried out various researches in order to develop a novel process for avoiding the use of the compound of Formula (II), i.e., the intermediate that is unstable, difficult to handle, and causes formation of the structural isomeric impurity. As the results thereof, the present inventors has developed a novel process which comprises forming a pyrimidine ring from a substituted phenylguanidine derivative or its salt, activating the pyrimidine ring to prepare a novel intermediate, and reacting the novel intermediate with (S)-3-acetamidopyrrolidine. It has been found that said process can solve the problems of the prior art methods and is suitable for industrial mass production.

And also, the present inventors have isolated novel crystalline forms of a hydrochloride of the compound of Formula 1; and found that said crystalline forms exhibit remarkably excellent stability, in comparison with the amorphous form according to the prior art.

Therefore, it is an object of the present invention to provide a process for preparing a diaminopyrimidine derivative or acid addition salt thereof, the process comprising the use of a novel intermediate.

And also, it is another object of the present invention to provide the novel intermediate and processes for preparing the same.

And also, it is still another object of the present invention to provide crystalline forms of a hydrochloride of the compound of Formula 1 and processes for preparing the same.

Technical Solution

In accordance with an aspect of the present invention, there is provided a process for preparing a compound of Formula 1 or acid addition salt thereof, comprising (a) reacting a compound of Formula 2 or salt thereof with (S)-3-acetamidopyrrolidine to prepare a compound of Formula 1; and optionally (b) reacting the compound of Formula 1 with an acid to prepare an acid addition salt of the compound of Formula 1:

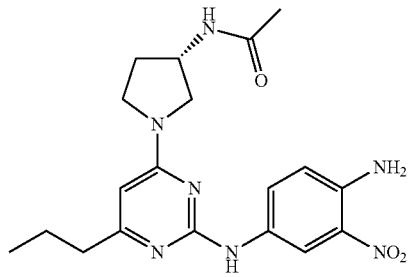

<Formula 1>

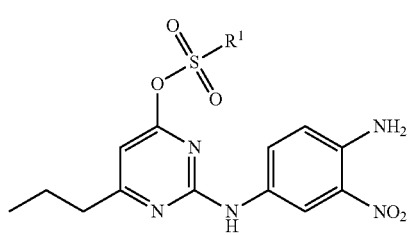

<Formula 2> wherein, $R^1$ is a $C_1$~$C_3$ alkyl group; or a phenyl group optionally substituted with one or more substituents selected from the group consisting of halogen, $C_1$~$C_3$ alkyl, and cyano.

In accordance with another aspect of the present invention, there is provided a compound of Formula 2 or salt thereof:

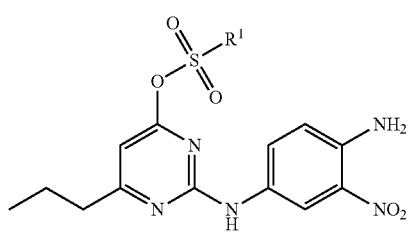

<Formula 2> wherein, $R^1$ is the same as defined in the above.

In accordance with still another aspect of the present invention, there is provided a process for preparing a compound of Formula 2 or salt thereof comprising (i) reacting a compound of Formula 5 or salt thereof with methyl 3-oxo-hexanoate to prepare a compound of Formula 4; (ii) reacting the compound of Formula 4 with $R^1$-sulfonyl halide to prepare a compound of Formula 2; and optionally (iii) converting the compound of Formula 2 to a salt thereof:

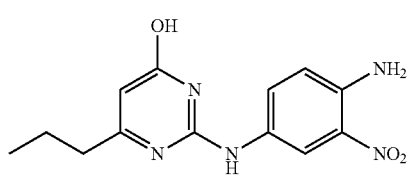

<Formula 4>

-continued

<Formula 5>

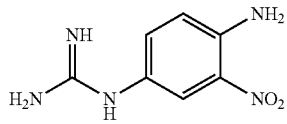

In accordance with still another aspect of the present invention, there is provided a crystalline form A of a hydrochloride of the compound of Formula 1, having an XRPD pattern with peaks at 7.4, 9.1, 12.0, 12.5, 13.5, 14.1, 15.9, 16.8, 18.3, 19.1, 24.6, 25.3 and 26.8° 2θ±0.2° 2θ.

<Formula 1>

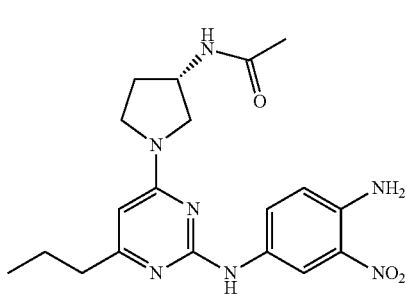

In accordance with still another aspect of the present invention, there is provided a process for preparing the crystalline form A of a hydrochloride of the compound of Formula 1, the process comprising (p) refluxing a reaction mixture obtained by adding hydrochloric acid to a compound of Formula 1 in an organic solvent; (q) cooling the reaction mixture obtained from Step (p) to form a precipitate; and (r) isolating the precipitate of Step (q).

In accordance with still another aspect of the present invention, there is provided a crystalline form B of a hydrochloride of the compound of Formula 1, having an XRPD pattern with peaks at 7.3, 8.8, 11.8, 12.5, 13.2, 13.6, 14.5, 17.7, 18.6, 19.6, 22.0, 24.9, 25.2, and 25.9° 2θ±0.2° 2θ.

<Formula 1>

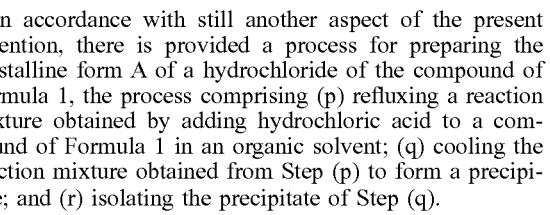

In accordance with still another aspect of the present invention, there is provided a process for preparing the crystalline form B of a hydrochloride of the compound of Formula 1, the process comprising exposing the crystalline form A of a hydrochloride of the compound of Formula 1 to a 40% or more relative humidity condition so as to control the water contents thereof to about 3.5% or more.

Advantageous Effects

The process of the present invention is carried out, by using a novel intermediate, i.e., the compound of Formula 2 or salt thereof, from a substituted phenylguanidine derivative or its salt. Therefore, the process of the present invention can avoid the use of the compound of Formula (II), i.e., the intermediate that is unstable, difficult to handle, and causes formation of the structural isomeric impurity. And also, the process of the present invention can provide the compound of Formula 1 or acid addition salt thereof in high yield and purity and be suitably applied to industrial mass production. In addition, the novel crystalline forms of a hydrochloride of the compound of Formula 1, i.e., the crystalline forms A and B, exhibit remarkably excellent stability, in comparison with the amorphous form according to the prior art.

BEST MODE

Figure 1:
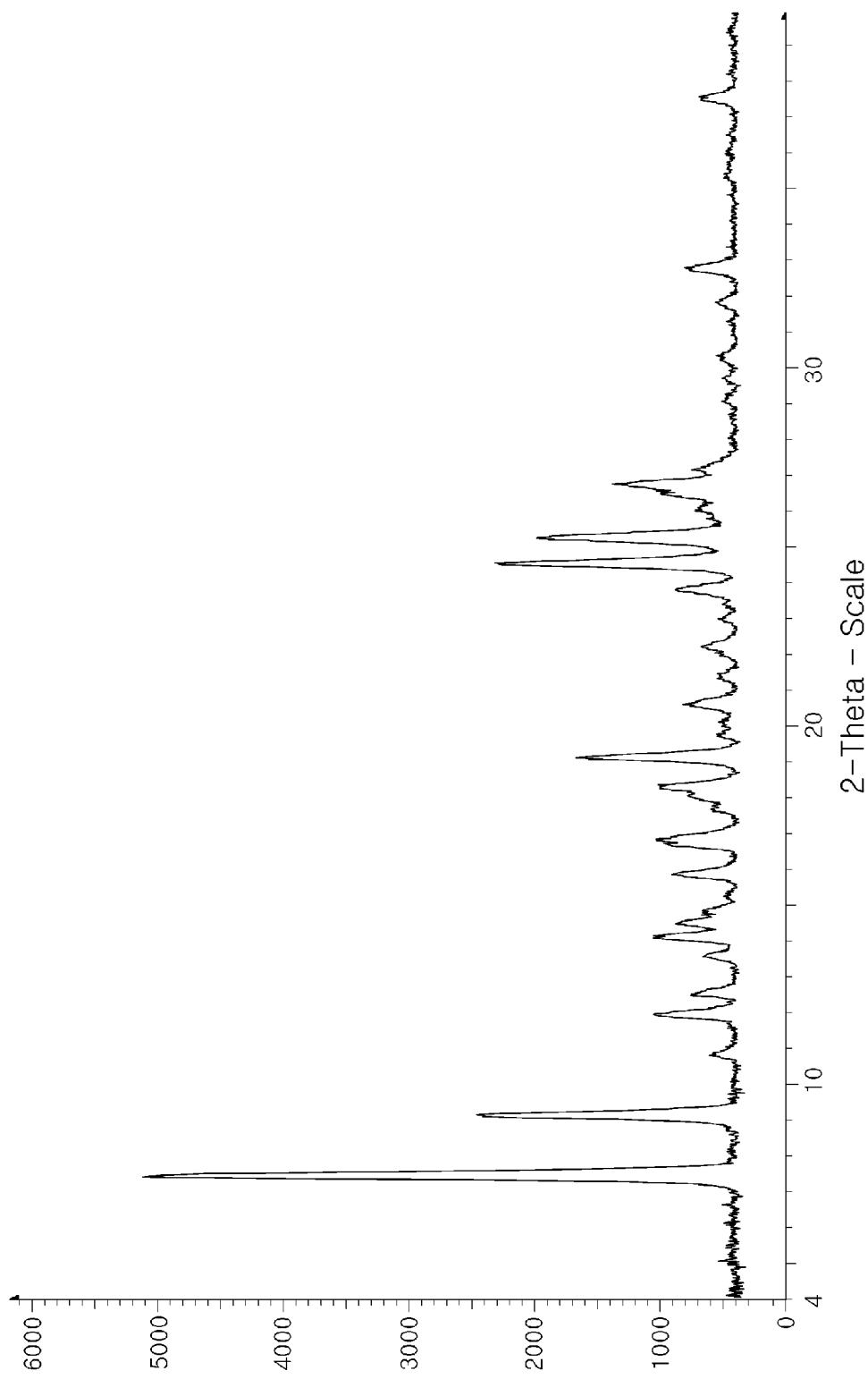
FIG. 1 shows an XRPD spectrum of the crystalline form A of a hydrochloride of the compound of Formula 1.

The present invention provides a process for preparing a compound of Formula 1 or acid addition salt thereof, comprising (a) reacting a compound of Formula 2 or salt thereof with (S)-3-acetamidopyrrolidine to prepare a compound of Formula 1; and optionally (b) reacting the compound of Formula 1 with an acid to prepare an acid addition salt of the compound of Formula 1:

<Formula 1>

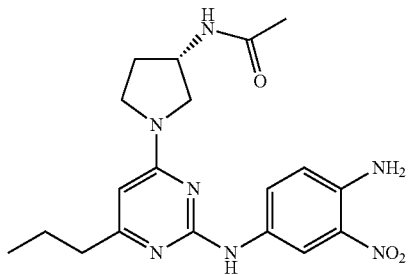

<Formula 2>

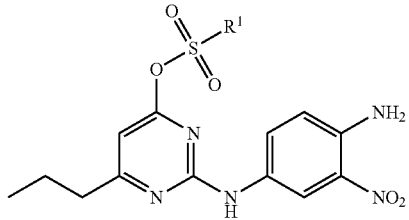

wherein, $R^1$ is a $C_1$~$C_3$ alkyl group; or a phenyl group optionally substituted with one or more substituents selected from the group consisting of halogen, $C_1$~$C_3$ alkyl, and cyano.

In the process of the present invention, (S)-3-acetamidopyrrolidine, one of the reactants, is a known compound and commercially available. And also, (S)-3-acetamidopyrrolidine may be formed by deprotecting the amino-protecting group from the commercially available compound of Formula 3 below.

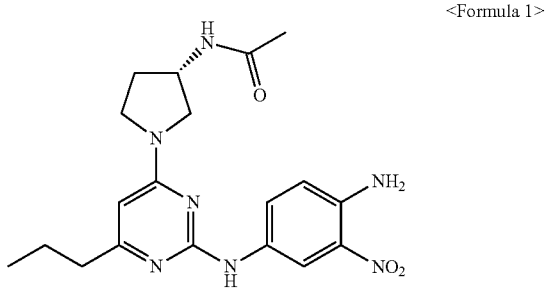 [SMILES: CCCc1cc(N2CC[C@H](NC(C)=O)C2)nc(Nc2ccc(N)c([N+](=O)[O-])c2)n1]

<Formula 3>

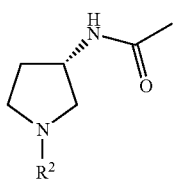

wherein, R² is a amino-protecting group such as t-butoxycarbonyl.

The deprotection may be carried out with one or more acids selected from the group consisting of hydrochloric acid, sulfuric acid, phosphoric acid, nitric acid, acetic acid, formic acid, sulfonic acid, p-toluenesulfonic acid, and methanesulfonic acid, preferably with p-toluenesulfonic acid or hydrochloric acid. The deprotection may be carried out in one or more solvents selected from the group consisting of dichloromethane, dichloroethane, N,N-dimethylformamide, dimethylacetamide, dimethyl sulfoxide, tetrahydrofuran, ethyl acetate, and toluene, preferably in toluene. And also, the deprotection may be carried out at the temperature ranging from 0° C. to 40° C., preferably from 10° C. to 30° C.

In an embodiment, the deprotection and the reaction of the formed (S)-3-acetamidopyrrolidine with a compound of Formula 2 or salt thereof may be carried out in a one-pot reaction. That is, in the process of the present invention, Step (a) may include (a1) deprotecting the compound of Formula 3 to form (S)-3-acetamidopyrrolidine; and (a2) performing a reaction through adding a compound of Formula 2 or salt thereof to the reaction mixture of Step (a1). The reaction of a compound of Formula 2 or salt thereof with (S)-3-acetamidopyrrolidine may be carried out in the presence of a base. The base may be one or more selected from the group consisting of potassium tert-butoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine, and diisopropylethylamine. Preferably, the base may be triethylamine or diisopropylethylamine. More preferably, the base may be diisopropylethylamine. The reaction of a compound of Formula 2 or salt thereof with (S)-3-acetamidopyrrolidine may be carried out at the temperature ranging from 40° C. to 130° C., preferably from 80° C. to 90° C.

In the process of the present invention, the acid used in Step (b) may be a conventional inorganic or organic acid suitable for forming a desired acid addition salt. Preferably, the acid used in Step (b) may be hydrochloric acid. When hydrochloric acid is used in Step (b), the product is obtained in the form of a hydrochloride of the compound of Formula 1.

In the process of the present invention, the compound of Formula 2 or salt thereof may be prepared or formed by a process comprising (i) reacting a compound of Formula 5 or salt thereof with methyl 3-oxohexanoate to prepare a compound of Formula 4; (ii) reacting the compound of Formula 4 with R¹-sulfonyl halide to prepare a compound of Formula 2; and optionally (iii) converting the compound of Formula 2 to a salt thereof:

<Formula 4>

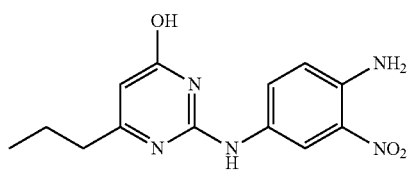

<Formula 5>

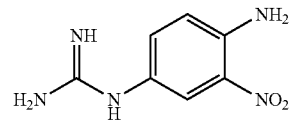

In the reaction of Step (i), the compound of Formula 5 may be prepared by reacting 4-amino-2-nitroaniline with cyanamide under an acidic condition, according to known methods, e.g., U.S. Pat. No. 6,562,854 B2 and so on. The salt of the compound of Formula 5 may in the form of 1-(4-amino-3-nitrophenyl)guanidine hemicarbonate. The reaction of Step (i), i.e., cyclization reaction, may be carried out in C₁~C₅ alcohol, preferably in n-butanol. And also, said cyclization reaction may be carried out at the temperature ranging from 50° C. to 130° C., preferably from 90° C. to 120° C.

The reaction of Step (ii), i.e., the reaction of the compound of Formula 4 and R¹-sulfonyl halide, may be carried out in the presence of a base. The base may be one or more selected from the group consisting of potassium tert-butoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine, and diisopropylethylamine. Preferably, the base may be triethylamine. The reaction of the compound of Formula 4 with R¹-sulfonyl halide may be carried in the presence of or in the absence of a solvent. When the reaction is carried out in presence of a solvent, the solvent may be one or more selected from the group consisting of acetone, methylethylketone, dichloromethane, dichloroethane, N,N-dimethylformamide, dimethylacetamide, dimethyl sulfoxide, tetrahydrofuran, C₁~C₅ alcohol, ethyl acetate, and toluene. And also, the reaction of the compound of Formula 4 with R¹-sulfonyl halide may be carried at the temperature ranging from 0° C. to 60° C. If necessary, the compound of Formula 2 obtained from the reaction of the compound of Formula 4 with R¹-sulfonyl halide may be additionally converted to a salt form thereof (e.g., to the form of an acid addition salt), by reacting with an acid such as hydrochloric acid, sulfuric acid, phosphoric acid, nitric acid, acetic acid, formic acid, or sulfonic acid. The obtained compound of Formula 2 or salt thereof may be isolated. And also, the obtained compound of Formula 2 or salt thereof may be directly used in the subsequent reaction, i.e., in the reaction with (S)-3-acetamidopyrrolidine, without the isolation thereof. In an embodiment, the reaction mixture of Step (ii) may be directly used in the reaction of Step (a), without isolating the compound of Formula 2 or salt thereof.

An example of the overall reaction steps of the present invention is shown in Reaction Scheme 2 below.

<Reaction Scheme 2>

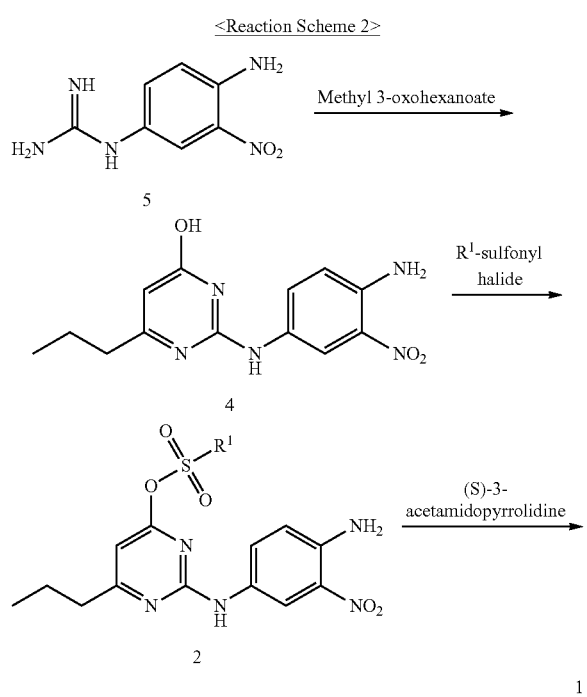

In the Reaction Scheme 2, R¹ is the same as defined in the above.

The present invention also provides a compound of Formula 2 or salt thereof useful for preparing the compound of Formula 1 or acid addition salt thereof:

<Formula 2>

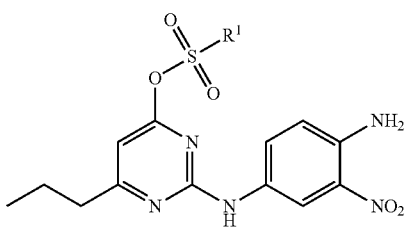

wherein, R¹ is the same as defined in the above.

The present invention also provides a process for preparing the compound of Formula 2 or salt thereof. That is, the present invention provides a process for preparing the compound of Formula 2 or salt thereof comprising (i) reacting a compound of Formula 5 or salt thereof with methyl 3-oxohexanoate to prepare a compound of Formula 4; (ii) reacting the compound of Formula 4 with R¹-sulfonyl halide to prepare a compound of Formula 2; and optionally (iii) converting the compound of Formula 2 to a salt thereof:

<Formula 4> 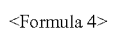

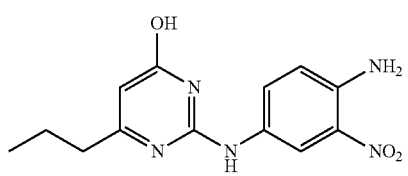

<Formula 5>

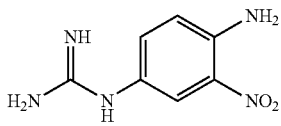

The reactions of Steps (i) and (ii) are as described in the above.

The present invention also provides novel crystalline forms of a hydrochloride of the compound of Formula 1 having excellent stability.

In an aspect, the present invention provides a crystalline form A of a hydrochloride of the compound of Formula 1, having an XRPD pattern with peaks at 7.4, 9.1, 12.0, 12.5, 13.5, 14.1, 15.9, 16.8, 18.3, 19.1, 24.6, 25.3 and 26.8° 2θ±0.2° 2θ.

<Formula 1>

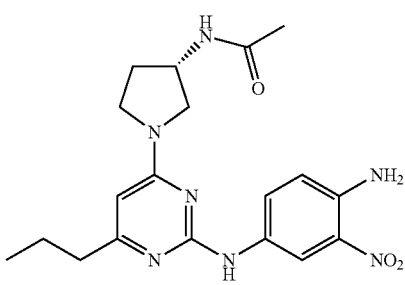

Preferably, the crystalline form A of a hydrochloride of the compound of Formula 1 may have the XRPD pattern of FIG. 1. And also, the crystalline form A of a hydrochloride of the compound of Formula 1 may have a differential scanning calorimetry (DSC) thermogram showing an endothermic peak at between 229° C. and 235° C., preferably at 232±2° C. The onset temperature may be 230±2° C.

The present invention also includes, within its scope, a process for preparing the crystalline form A of a hydrochloride of the compound of Formula 1. Specifically, the present invention provides a process for preparing the crystalline form A of a hydrochloride of the compound of Formula 1, the process comprising (p) refluxing a reaction mixture obtained by adding hydrochloric acid to a compound of Formula 1 in an organic solvent; (q) cooling the reaction mixture obtained from Step (p), typically to room temperature, to form a precipitate; and (r) isolating the precipitate of Step (q). The organic solvent in Step (p) may be one or more selected from the group consisting of acetone, methylethylketone, ethyl acetate, acetonitrile, tetrahydrofuran, heptane, and $C_1$~$C_5$ alcohol. For example, a mixed solvent of acetone and isopropyl alcohol may be used as the organic solvent. The ratio (volumetric ratio) of acetone and isopropyl alcohol in the mixed solvent may be in the range of 200~280:100, preferably in the range of about 250:100. The refluxing may be carried out at the temperature ranging from 50° C. to 120° C., preferably from 55° C. to 70° C.

In another aspect, the present invention provides a crystalline form B of a hydrochloride of the compound of Formula 1, having an XRPD pattern with peaks at 7.3, 8.8, 11.8, 12.5, 13.2, 13.6, 14.5, 17.7, 18.6, 19.6, 22.0, 24.9, 25.2, and 25.9° 2θ±0.2° 2θ.

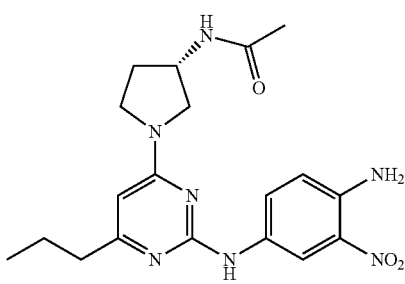
<Formula 1>

Figure 2:
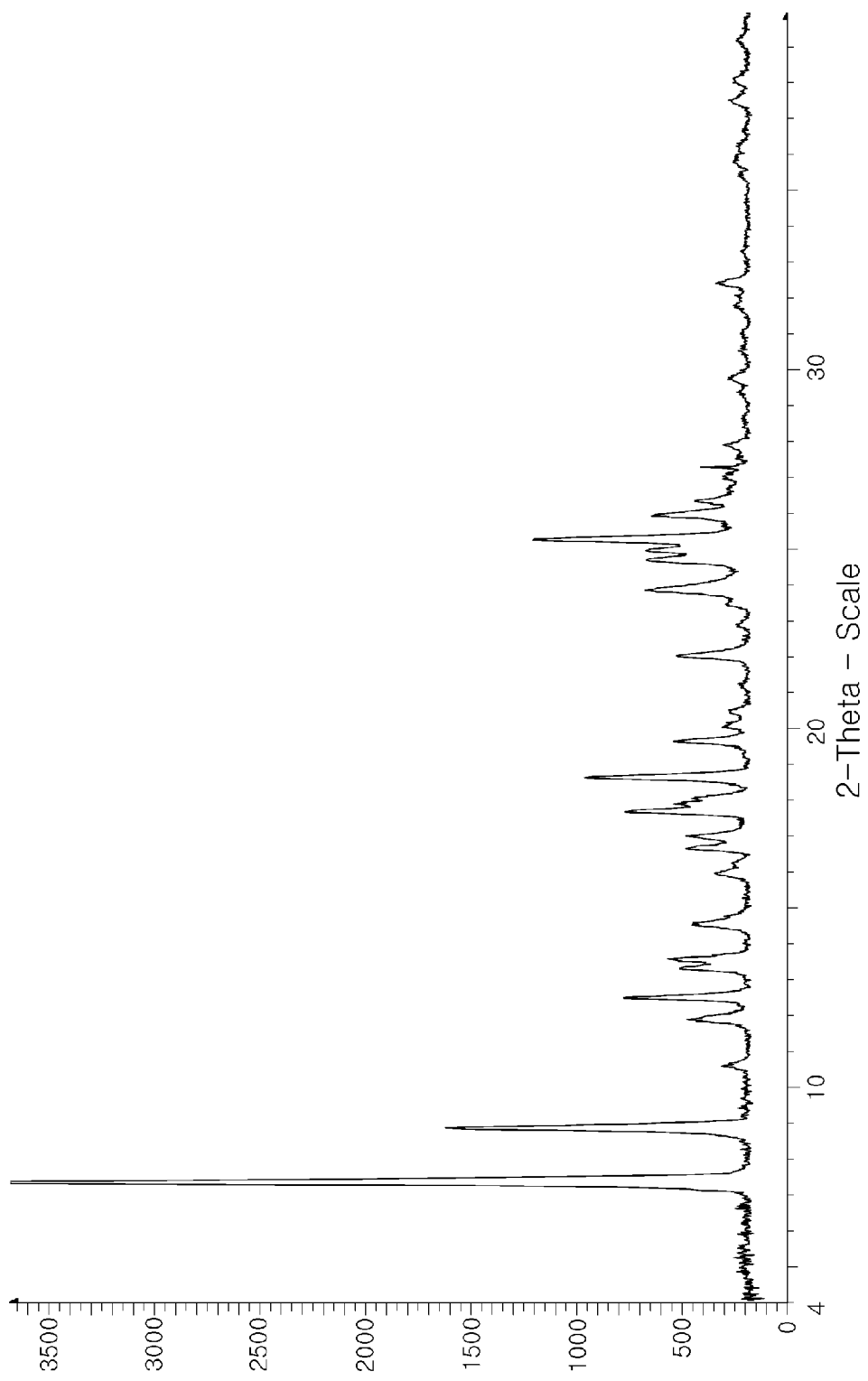
FIG. 2 shows an XRPD spectrum of the crystalline form B of a hydrochloride of the compound of Formula 1.

Preferably, the crystalline form B of a hydrochloride of the compound of Formula 1 may have the XRPD pattern of FIG. 2. And also, the crystalline form B of a hydrochloride of the compound of Formula 1 may have a differential scanning calorimetry (DSC) thermogram showing an endothermic peak at between 229° C. and 235° C., preferably at 232±2° C. The onset temperature may be 230±2° C.

The present invention also includes, within its scope, a process for preparing the crystalline form B of a hydrochloride of the compound of Formula 1. Specifically, the present invention provides a process for preparing the crystalline form B of a hydrochloride of the compound of Formula 1, the process comprising exposing the crystalline form A of a hydrochloride of the compound of Formula 1 to a 40% or more relative humidity condition so as to control the water contents thereof to about 3.5% or more.

The present invention will be described in further detail with reference to the following examples. These examples are for illustrative purposes only and are not intended to limit the scope of the present invention.

Preparation Example 1:
1-(4-amino-3-nitrophenyl)guanidine hemicarbonate

A mixture of 4-amino-2-nitroaniline (100.0 g, 0.653 mol), purified water (200 mL), concentrated hydrochloric acid (61.2 g, 0.588 mol), and cyanamide (35.7 g, 0.849 mol) was stirred at 80-90° C. for 3 hours. A solution of sodium carbonate (41.5 g, 0.392 mol) in purified water (500 mL) was slowly added to the reaction mixture at about 65° C. The reaction mixture was stirred for 2 hours, cooled to about 10° C., and then filtered. The resulting solid was dried in vacuo to obtain 112.5 g of the titled compound. (Yield: 76.2%).

$^1$H-NMR (600 MHz, DMSO) δ 9.86 (br, 1H), 7.80 (s, 1H), 7.66 (s, 2H), 7.56 (s, 2H), 7.29 (s, 1H), 7.15 (s, 1H)

Example 1: 2-((4-amino-3-nitrophenyl)amino)-6-propylpyrimidin-4-ol

A mixture of 1-(4-amino-3-nitrophenyl)guanidine hemicarbonate (110.0 g, 0.486 mol), methyl 3-oxohexanoate (91.1 g, 0.632 mol), and n-butanol (330 mL) was stirred at 9° C. for 15 hours. The reaction mixture was cooled to room temperature and then filtered. The resulting solid was dried under reduced pressure to obtain 111.3 g of the titled compound. (Yield: 79.1%, HPLC purity: 98.2%)

$^1$H-NMR (400 MHz, DMSO) δ 10.82 (br, 1H), 8.98 (br, 1H), 8.57 (s, 1H), 7.49 (d, 1H), 7.30 (s, 2H), 7.02 (d, 1H), 5.62 (s, 1H), 2.35 (t, 2H), 1.72-1.63 (m, 2H), 0.91 (t, 3H)

Example 2: 2-((4-amino-3-nitrophenyl)amino)-6-propylpyrimidin-4-yl 4-methylbenzenesulfonate To a solution of 2-((4-amino-3-nitrophenyl)amino)-6-propylpyrimidin-4-ol (106.5 g, 0.368 mol) and p-toluenesulfonyl chloride (64.27 g, 0.337 mol) in acetone (700 mL), was added triethylamine (37.2 g, 0.368 mol). The reaction mixture was stirred at room temperature for 3 hours and then filtered. Toluene (1,065 ml) was added to the resulting filtrate, which was then concentrated to 430 ml so as to remove acetone. The resulting solution was directly used in the preparation of the compound of Formula 1. A portion of the solution was concentrated under reduced pressure for identification of the resulting product and the $^1$H-NMR spectrum data obtained therefrom are as follows.

$^1$H-NMR (400 MHz, DMSO) δ 9.73 (s, 1H), 8.33 (br, 1H), 7.90 (d, 2H), 7.56 (d, 1H), 7.43 (d, 2H), 7.32 (s, 2H), 6.96 (d, 1H), 6.44 (s, 1H), 2.59 (t, 2H), 2.40 (s, 3H), 1.74-1.65 (m, 2H), 1.18 (t, 3H)

Example 3: 4-methylbenzenesulfonic Acid Salt of 2-((4-amino-3-nitrophenyl)amino)-6-propylpyrimidin-4-yl 4-methylbenzenesulfonate To a solution of 2-((4-amino-3-nitrophenyl)amino)-6-propylpyrimidin-4-ol (20.0 g, 0.069 mol) and p-toluenesulfonyl chloride (14.5 g, 0.076 mol) in acetone (170 mL), was added triethylamine (8.4 g, 0.083 mol). The reaction mixture was stirred at room temperature for 3 hours and then filtered. p-Toluenesulfonic acid (14.5 g, 0.076 mol) was added to the resulting filtrate. The mixture was stirred at room temperature for 2 hours and then filtered. The resulting solid was dried under reduced pressure to obtain 37.9 g of the titled compound. (Yield: 89.1%)

$^1$H-NMR (400 MHz, CDCl$_3$) δ 11.70 (s, 1H), 8.31 (s, 1H), 7.81 (d, 2H), 7.66 (d, 2H), 7.56 (d, 1H), 7.43 (d, 2H), 7.32 (s, 2H), 6.96 (d, 1H), 6.44 (s, 1H), 2.59 (t, 2H), 2.40 (s, 3H), 1.74-1.65 (m, 2H), 1.18 (t, 3H)

Example 4: 2-((4-amino-3-nitrophenyl)amino)-6-propylpyrimidin-4-yl methanesulfonate To a solution of 2-((4-amino-3-nitrophenyl)amino)-6-propylpyrimidin-4-ol (18.0 g, 0.062 mol) and methanesulfonyl chloride (7.8 g, 0.068 mol) in N,N-dimethylformamide (54 mL), was added triethylamine (7.6 g, 0.075 mol). The reaction mixture was stirred at room temperature for 3 hours. Purified water (180 mL) and toluene (54 mL) were added to the reaction mixture, which was then filtered. The resulting solid was dried under reduced pressure to obtain 18.0 g of the titled compound. (Yield: 79.0%)

$^1$H-NMR (400 MHz, DMSO) δ 10.62 (br, 1H), 8.76 (br, 1H), 8.54 (s, 1H), 7.48 (d, 1H), 7.31 (s, 2H), 6.99 (d, 1H), 5.66 (s, 1H), 3.72 (s, 3H), 2.34 (t, 2H), 1.70-1.64 (m, 2H), 0.91 (t, 3H)

Example 5: 2-((4-amino-3-nitrophenyl)amino)-6-propylpyrimidin-4-yl 4-bromobenzenesulfonate To a solution of 2-((4-amino-3-nitrophenyl)amino)-6-propylpyrimidin-4-ol (10.0 g, 0.035 mol) and 4-bromobenzenesulfonyl chloride (9.7 g, 0.038 mol) in N,N-dimethylformamide (30 mL), was added triethylamine (4.2 g, 0.041 mol). The reaction mixture was stirred at room temperature for 3 hours. Purified water (180 mL) and toluene (54 mL) were added thereto. The extracted organic layer was directly used in the preparation of the compound of Formula 1. A portion of the organic layer was concentrated under reduced pressure for identification of the resulting product and the $^1$H-NMR spectrum data obtained therefrom are as follows.

¹H-NMR (400 MHz, DMSO) δ 9.72 (s, 1H), 7.96 (br, 2H), 7.83 (d, 2H), 7.56 (d, 1H), 7.27 (s, 2H), 6.98 (d, 1H), 6.47 (s, 1H), 2.59 (t, 2H), 1.74-1.65 (m, 2H), 0.90 (t, 3H)

Example 6: (S)—N-(1-(2-((4-amino-3-nitrophenyl)amino)-6-propylpyrimidin-4-yl)pyrrolidin-3-yl)acetamide To a mixture of tert-butyl (S)-3-acetamidopyrrolidine-1-carboxylate (70.0 g, 0.307 mol) and toluene (700 mL), was added p-toluenesulfonic acid monohydrate (116.7 g, 0.613 mol). The reaction mixture was stirred at room temperature for 6 hours. To the reaction mixture, were added a solution of 2-((4-amino-3-nitrophenyl)amino)-6-propylpyrimidin-4-yl 4-methylbenzenesulfonate in toluene obtained in Example 2 and diisopropylethylamine (198.1 g, 1.533 mol). The reaction mixture was stirred at 80-90° C. for 5 hours and then concentrated under reduced pressure. To the resulting residue, were added methanol (210 mL) and a 50% sodium bicarbonate solution (70 mL). The resulting mixture was stirred at room temperature for 2 hours and then distilled water (1,050 mL) was dropwise added thereto. After filtering the reaction mixture, the resulting solid was dried under reduced pressure to obtain 105.5 g of the titled compound. (Yield: 86.0%, HPLC purity: 99.1%)

¹H-NMR (400 MHz, DMSO) δ 8.99 (s, 2H), 8.17 (s, 1H), 7.58 (d, 1H), 7.16 (s, 2H), 6.93 (d, 1H), 5.79 (s, 1H), 4.35 (m, 1H), 3.70-3.35 (m, 6H), 2.40 (t, 2H), 1.82 (s, 3H), 1.71-1.65 (m, 2H), 0.92 (t, 3H)

Example 7: (S)—N-(1-(2-((4-amino-3-nitrophenyl)amino)-6-propylpyrimidin-4-yl)pyrrolidin-3-yl)acetamide Hydrochloride (Crystalline Form A)

To a mixture of (S)—N-(1-(2-((4-amino-3-nitrophenyl)amino)-6-propylpyrimidin-4-yl)pyrrolidin-3-yl)acetamide (10.0 g, 0.025 mol), acetone (250 mL), and isopropyl alcohol (100 mL), was added concentrated hydrochloric acid (2.6 g, 0.025 mol) at 50° C. The reaction mixture was refluxed under stirring for 20 hours, cooled to room temperature, and then filtered. The resulting solid was dried under reduced pressure at about 60° C. to obtain 9.8 g of the titled compound. (Yield: 90.0%, HPLC purity: 99.9%)

¹H-NMR (600 MHz) δ 8.56 (d, 1H), 7.37-7.34 (m, 1H), 6.96-6.93 (m, 1H), 6.09 (d, 1H), 4.53-4.47 (d, 1H), 3.91-3.43 (m, 4H), 2.62-2.58 (m, 2H), 2.36-2.28 (m, 1H), 2.12-2.05 (m, 1H), 1.98 (s, 3H), 1.78-1.74 (m, 2H), 1.06-1.03 (t, 3H)

The resulting product was subject to X-ray powder diffraction (XRPD) analysis. The X-Ray powder diffraction (XRPD) patterns were collected on a Bruker D8 Advance diffractometer using Cu—Kα radiation (λ=1.5406 A) and operating at 40 kV and 40 mA. The patterns were collected by scanning 2θ from 4 to 40 with increment of 0.02 and scan speed of 0.1 second per step (divergence slit: 0.3 and antiscatter slit: 0.3). The obtained XRPD spectrum is shown in FIG. 1, which shows characteristic peaks at 7.4, 9.1, 12.0, 12.5, 13.5, 14.1, 15.9, 16.8, 18.3, 19.1, 24.6, 25.3 and 26.8° 2θ±0.2° 2θ.

And also, the resulting product was subject to differential scanning calorimetry (DSC) analysis. The differential scanning calorimetry (DSC) analysis was carried out with the Mettler Toledo DSC 1 STAR Differential Scanning calorimeter. The analytical conditions thereof are as follows: sample was placed into an aluminum pan; the pan was covered with an aluminum lid (pinhole); 99% purged nitrogen gas (gas flow rate: 50 mL/min); start temperature 30° C.; end temperature 300° C.; and heating rate 10° C./min. As a result thereof, the endothermic peak was observed at between 229° C. and 235° C. The onset temperature was 230.4° C. and the maximum peak was observed at 233.0° C.

Example 8: (S)—N-(1-(2-((4-amino-3-nitrophenyl)amino)-6-propylpyrimidin-4-yl)pyrrolidin-3-yl)acetamide Hydrochloride (Crystalline Form B)

The crystalline form A of (S)—N-(1-(2-((4-amino-3-nitrophenyl)amino)-6-propylpyrimidin-4-yl)pyrrolidin-3-yl) acetam ide hydrochloride prepared in Example 7 was exposed in a wet chamber having 40% relative humidity, for 5 hours or more, to obtain the titled compound.

¹H-NMR (600 MHz) δ 8.56 (d, 1H), 7.37-7.34 (m, 1H), 6.96-6.93 (m, 1H), 6.09 (d, 1H), 4.53-4.47 (d, 1H), 3.91-3.43 (m, 4H), 2.62-2.58 (m, 2H), 2.36-2.28 (m, 1H), 2.12-2.05 (m, 1H), 1.98 (s, 3H), 1.78-1.74 (m, 2H), 1.06-1.03 (t, 3H)

The resulting product was subject to X-ray powder diffraction (XRPD) analysis and differential scanning calorimetry (DSC) analysis, according to the same methods as in Example 7. The obtained XRPD spectrum is shown in FIG. 2, which shows characteristic peaks at 7.3, 8.8, 11.8, 12.5, 13.2, 13.6, 14.5, 17.7, 18.6, 19.6, 22.0, 24.9, 25.2, and 25.9° 2θ±0.2° 2θ. As a result of the differential scanning calorimetry (DSC) analysis, the endothermic peak was observed at between 229° C. and 235° C. The onset temperature was 229.4° C. and the maximum peak was observed at 232.2° C.

Experimental Example 1: Stability Tests (S)—N-(1-(2-((4-amino-3-nitrophenyl)amino)-6-propylpyrimidin-4-yl)pyrrolidin-3-yl) acetamide hydrochloride prepared according to WO 2012/115480 (Amorphous form, Test compound 1) and the crystalline form A of (S)—N-(1-(2-((4-amino-3-nitrophenyl)amino)-6-propylpyrimidin-4-yl)pyrrolidin-3-yl)acetam ide hydrochloride prepared in Example 7 (Test compound 2) were stored under the conditions of 60° C. and 75% RH for 2 weeks. The amounts of each test compound and the deacetylated impurities were analyzed with HPLC so as to measure the respective HPLC purities. The results thereof are shown in Table 1 below.

TABLE 1

| | | HPLC purities | | |
|---|---|---|---|---|
| | | | Storage time | |
| Test compound | | Initial | 1 week | 2 weeks |
| Test compound 1 (Amorphous form) | Compound | 98.7% | 95.5% | 86.6% |
| | Deacetylated impurities | 0.58% | 3.78% | 12.7% |
| Test compound 2 (Crystalline form A) | Compound | 99.6% | 99.6% | 99.6% |
| | Deacetylated impurities | 0.08% | 0.07% | 0.07% |

As shown in Table 1 above, the crystalline form A according to the present invention exhibited not only high purity from the initial, but also no significant change in the HPLC purity and the amount of deacetylated impurities under the conditions of 60° C. and 75% RH. On the contrary, the amorphous form according to the prior art exhibited not only high level of deacetylated impurities from the initial, but also marked decrease in the HPLC purity and the marked increase in the amount of deacetylated impurities under the conditions of 60° C. and 75% RH. Therefore, from the above results, it can be confirmed that the crystalline form according to the present invention has excellent stability.

The invention claimed is:

1. A process for preparing a compound of Formula 1 or acid addition salt thereof, comprising (a) reacting a compound of Formula 2 or salt thereof with (S)-3-acetamidopyrrolidine to prepare a compound of Formula 1; and optionally (b) reacting the compound of Formula 1 with an acid to prepare an acid addition salt of the compound of Formula 1:

<Formula 1>

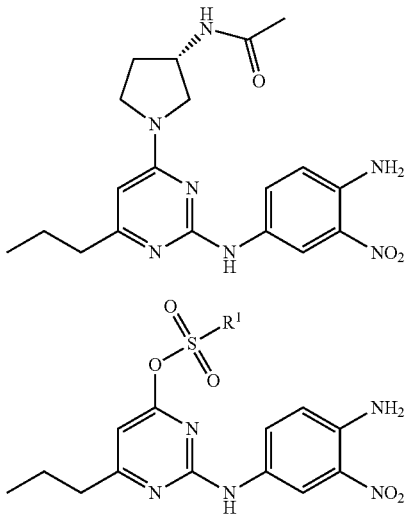

<Formula 2>

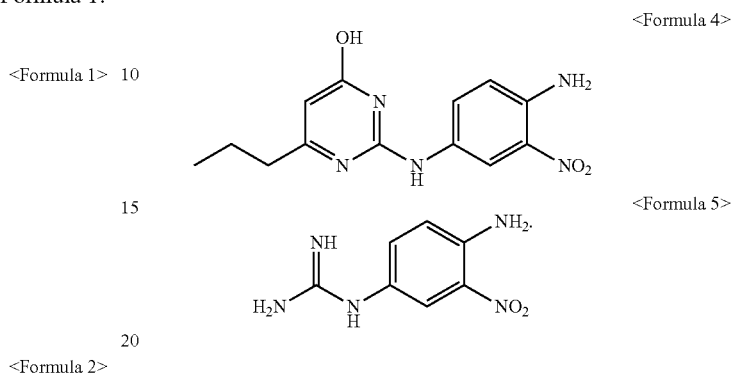

wherein, $R^1$ is a $C_1$~$C_3$ alkyl group; or a phenyl group optionally substituted with one or more substituents selected from the group consisting of halogen, $C_1$~$C_3$ alkyl, and cyano.

2. The process according to claim 1, wherein the reaction of a compound of Formula 2 or salt thereof with (S)-3-acetamidopyrrolidine is carried out in the presence of a base.

3. The process according to claim 2, wherein the base is one or more selected from the group consisting of potassium tert-butoxide, sodium hydroxide, potassium hydroxide, sodium hydride, sodium carbonate, potassium carbonate, potassium phosphate, sodium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine, and diisopropylethylamine.

4. The process according to claim 1, wherein the acid used in Step (b) is hydrochloric acid.

5. The process according to claim 1, wherein the compound of Formula 2 or salt thereof is prepared or formed by a process comprising (i) reacting a compound of Formula 5 or salt thereof with methyl 3-oxohexanoate to prepare a compound of Formula 4; (ii) reacting the compound of Formula 4 with $R^1$-sulfonyl halide, wherein R1 is the same as defined in claim 1, to prepare a compound of Formula 2; and optionally (iii) converting the compound of Formula 2 to a salt thereof:

<Formula 4>

<Formula 5>

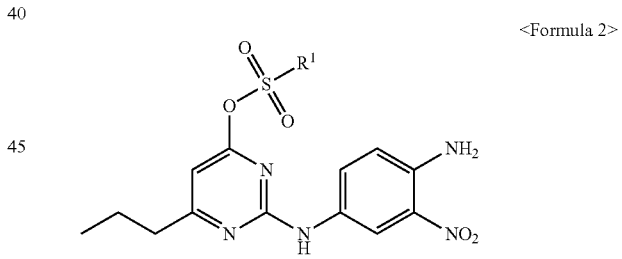

6. The process according to claim 5, wherein the reaction of the compound of Formula 4 with $R^1$-sulfonyl halide is carried out in the presence of a base.

7. The process according to claim 6, wherein the base is one or more selected from the group consisting of potassium tert-butoxide, sodium hydroxide, potassium hydroxide, sodium hydride, sodium carbonate, potassium carbonate, potassium phosphate, sodium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine, and diisopropylethylamine.

8. The process according to claim 5, wherein the reaction mixture of Step (ii) is directly used in the reaction of Step (a), without isolating the compound of Formula 2 or salt thereof.

9. A compound of Formula 2 or salt thereof:

<Formula 2> wherein, $R^1$ is the same as defined in claim 1.

* * * * *